US006448047B2

(12) United States Patent
Dattagupta et al.

(10) Patent No.: US 6,448,047 B2
(45) Date of Patent: *Sep. 10, 2002

(54) SAMPLE PROCESSING TO RELEASE NUCLEIC ACIDS FOR DIRECT DETECTION

(75) Inventors: Nanibhushan Dattagupta; C. Nagaraja Sridhar; Whei-Kuo Wu, all of San Diego, CA (US)

(73) Assignee: Applied Gene Technologies, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/846,603

(22) Filed: Apr. 30, 2001

Related U.S. Application Data

(63) Continuation of application No. 09/385,624, filed on Aug. 26, 1999, now Pat. No. 6,242,188.
(60) Provisional application No. 60/146,579, filed on Jul. 30, 1999.

(51) Int. Cl.[7] ............... C12P 15/64; C12Q 1/68; C12N 1/00; C12N 1/06
(52) U.S. Cl. ............ 435/91.1; 435/6; 435/91.2; 435/243; 435/259
(58) Field of Search ............ 435/6, 91.1, 91.2, 435/243, 259

(56) References Cited

U.S. PATENT DOCUMENTS

| | | | |
|---|---|---|---|
| 4,395,486 A | 7/1983 | Wilson et al. | 435/6 |
| 4,582,789 A | 4/1986 | Sheldon, III et al. | 435/6 |
| 4,683,195 A | 7/1987 | Mullis et al. | 435/91 |
| 4,683,202 A | 7/1987 | Mullis et al. | 435/6 |
| 4,734,454 A | 3/1988 | Dattagupta | 435/6 |
| 5,010,183 A | 4/1991 | Macfarlane | 536/27 |
| 5,026,840 A | 6/1991 | Dattagupta et al. | 536/27 |
| 5,221,608 A | 6/1993 | Cimino et al. | 435/6 |
| 5,348,855 A * | 9/1994 | Dattagupta et al. | 435/6 |
| 5,371,003 A | 12/1994 | Murry et al. | 435/172.3 |
| 5,409,818 A | 4/1995 | Davey et al. | 435/91.21 |
| 5,554,517 A | 9/1996 | Davey et al. | 435/91.21 |
| 5,599,660 A | 2/1997 | Landegren et al. | 435/4 |
| 5,792,614 A | 8/1998 | Western et al. | 435/6 |
| 5,837,452 A * | 11/1998 | Clark et al. | 435/6 |
| 6,242,188 B1 * | 6/2001 | Dattagupta et al. | 435/6 |

FOREIGN PATENT DOCUMENTS

| | | |
|---|---|---|
| EP | 0512 334 A | 11/1992 |
| EP | 0671473 | 9/1995 |
| EP | 0684 316 A | 11/1995 |
| EP | 0747351 | 12/1996 |
| WO | WO 92/00983 | 1/1992 |
| WO | 92/07957 | 5/1992 |
| WO | WO 96/40900 | 12/1996 |
| WO | WO 99/18933 | 4/1999 |
| WO | WO 01/10413 | 2/2001 |

OTHER PUBLICATIONS

Clontech Catalog No. 8480–1, 2001.*
Clontech Catallog No. 8480–2, 2001.*
Erlich (E.), PCR Technology, Principles and Applications for DNA Amplification, p. 20, Table 1, 1989.*
Sigma Aldrich Catalog No. P2308, 2001.*
Su, W.–J. et al. (2000) Clin. Med J. 63:521–525.*
Chaires, et al. (1996). Biochem 35:2047–2053.
Chaires, et al. (1977). J. Med Chem40:261–266.
Cimino, et al. (1990). Nucleic Acid Res 19(1):99–107.
Clarke. (1981). Biochim Biophys Acta 670(2):195–202.
Dattagupta, et al. (G.G. JAckson, H.D. Schlumberger and H.J. Zeiler, Eds.) Friedr. Vieweg & Sohn Verlagsgesellshaft mbH, Braunschweig, 241–247 (1989).
Della–Latta, et al. (1998). Am J Clin Pathol 110:301–310.
Favilla et al. (1997). Biophys Chem 67(13)75–83.
Gelmini, et al. (1997). Clin Chem (43(5):752–758.
Haq, et al. (1997). J Mol Biol 271:244–257.
Heim, et al. (1998). Nucleic Acid Res 26(9):2250–2251.
Hu, et al. (1996). Diagn Microbiol Infect Dis 24:71–76.
Lacks and Springhorn. (1980). J Biol Chem 255(15);7467–7473.
Marmur. (1961). J Mol Biol 3:208–218.
McIntyre and Stark. (1988). Anal Biochem 174(1):209–214.
Moore, et al. (1998) J Clin Microbiol 36(4):1028–1031.
Nazarenko, et al. (1997). Nucleic Acid Res 25(12):2516–2521.
Neumaier, et al. (1998). Clin Chem 44(1):12–26.
Oehlenschlager, et al. (1996). Proc Natl Acad Sci USA 93:12811–12816.
Pao, et al. (1993). Mol and Cell Probes &:217–219.
Prajapati, et al. (1998). Eur J Biochem 255(1)178–184. Abstract only.
Rys, et al. (1993). J Clin Micribiol 31(9):2356–2360.
Sambrook, et al. Molecular Cloning A Laboratory Manual (2nd Ed.) Cold Spring Harbor Laboratory Press (1989), pp. 5.34–5.35.
Stryer. Biochemistry (3rd Ed.), p. 215.
Tevere, et al. (1996). J Clin Micribiol 34(4):918–923.
Troesch, et al. (1999). J Clin Micribiol 37(1):49–55.
Vaneechoutte, et al. (1997). J Med Microbiol 46:188–194.
Walder, et al. (1993). Nucleic Acid Res 21(18):4339–4343.
Walker, et al. (1992). Nucleic Acid Res 20(7):1691–1696.
Whelen, et al. (1995). J Clin Micribiol 33(3):556–561.
Wylie, et al. (1998). J Clin Micribiol 36(12):3488–3491.
Bianchi, N. et al.(1999) Drug Development Research 46 (2):96–106.
Database accession No. 1998323380 XP 002179558.
Database accession No. PREV199800351691 XP 002179616.
Database accession No. PREV199598359327 XP 002179617.

* cited by examiner

Primary Examiner—Jezia Riley
(74) Attorney, Agent, or Firm—Morrison & Foerster LLP

(57) ABSTRACT

The present invention describes compositions and methods for releasing nucleic acids from cells in a form that is suitable for labeling/capture, amplification, or detection in a single reagent addition step. The compositions include a lipid, membrane fluidizing compound, enzyme for degrading cell structure, metal chelators, or one or more nucleic acid probes or primers complementary to the nucleic acid to be detected. The compositions are non-denaturing and non-inhibitory of enzymes or proteins that are used in nucleic acid release, amplification, labeling or detection. The invention also provides kits for performing the above methods.

11 Claims, No Drawings

SAMPLE PROCESSING TO RELEASE NUCLEIC ACIDS FOR DIRECT DETECTION

This application is a continuation of Ser. No. 09/385,624, filed Aug. 26, 1999, now U.S. Pat. No. 6,242,188, which claims the benefit of the priority date of the U.S. Provisional Patent Application Serial No. 60/146,579, filed Jul. 30, 1999 under 35 U.S.C. §119(e). The content of the above-referenced applications is herein incorporated by reference in its entirety.

FIELD OF THE INVENTION

This invention relates to the field of nucleic acid detection and, more specifically, to the processing of samples to release nucleic acids in a condition suitable for direct detection.

BACKGROUND OF THE INVENTION

Nucleic acid detection through modern molecular biological techniques has revolutionized diagnosis of infections, cancer, inborn genetic errors, HLA typing, and forensic and paternity testing. Methods to detect nucleic acids commonly requires several sample processing steps, including use of a lysis reagent to lyse cells and release the nucleic acids contained within the cells. Lysis reagents typically consist of a strong detergent such as sodium dodecyl sulfate and alkaline pH conditions.

The need for multiple processing steps when using a lysis reagent, such as one containing a strong detergent, primarily results from inhibitors of later nucleic acid detection steps that are present or associated with the lysis reagent. The inhibitors must be neutralized or removed before amplification or other additional steps in nucleic acid detection can proceed. These additional steps result in increased labor and materials costs for the clinical laboratory. Use of a lysis reagent for nucleic acid detection also is detrimental because it can, under some circumstances, degrade the nucleic acids, thereby decreasing sensitivity in some assay formats. Thus, a need exists for an approach to isolate nucleic acids from a cell sample that avoids the additional steps associated with lysis reagents and allows for release and detection from a single reagent addition step.

SUMMARY OF THE INVENTION

Accordingly, it is an object of the present invention to eliminate the additional processing steps and degradation associated with nucleic acid lysis procedures. This is achieved by using lipids that are non-denaturing for enzymes and proteins required in further processing steps.

It is also an object of the present invention to provide compositions for releasing nucleic acid from cells or samples that include reagents for labeling or performing amplification such that release and detection of nucleic acid can be performed by a single reagent addition step.

To accomplish these and other objectives, there has been provided, according to one aspect of the present invention, a composition comprising an aqueous solution for releasing nucleic acid from a sample for direct detection, comprising one or more lipids and, one or more of: i) an enzyme(s) to degrade cell structure; ii) a non-ionic membrane fluidizing compound(s); and iii) a metal chelator(s). The aqueous solution is non-inhibitory of enzymes or proteins that are used in nucleic acid release, amplification, labeling or detection, and can include one or more nucleic acid probes or primers complementary to the nucleic acid to be detected.

According to one embodiment of the present invention, the lipids of the aqueous solution comprise lipids in the form of liposomal vesicles or other structure for encapsulating the aqueous solution.

According to another embodiment of the present invention, the aqueous solution includes reagents for labeling nucleic acid. Such reagents comprise a compound comprising a photoactivatible binding ligand, a label comprising a detectable moiety and, optionally, a nucleic acid binding enhancer moiety.

According to yet another embodiment of the present invention, the aqueous solution further comprises one or more nucleic acid probes or primers complementary to the nucleic acid to be detected.

According to still yet another embodiment of the present invention, the one or more lipids of the aqueous solution comprise 3-(2-aminopropyl-1,3-dihexadecyloxypropyl) hexadecyl ether, 3-(2aminopropyl-1-octadecyloxy-3-benzyloxypropyl) benzyl sulfide, or bis(3-benzyloxypropyl-1-octadecyloxy-3-benzyloxy-2-propyl amine)-polyethyleneglycol.

In another aspect of the present invention, there is provided a composition comprising an aqueous solution comprising one or more membrane fluidizing compounds for releasing nucleic acid and one or more of: i) an enzyme(s) to degrade cell structure; ii) a lipid(s); and iii) a metal chelator(s). The aqueous solution is non-denaturing and non-inhibitory of enzymes or proteins that are used in nucleic acid release, amplification, labeling or detection.

According to one embodiment of the present invention, the lipids of the aqueous solution comprise lipids in the form of liposomal vesicles or other structure for encapsulating the aqueous solution.

According to another embodiment of the present invention, the aqueous solution includes reagents for labeling nucleic acid. Such reagents comprise a compound comprising a photoactivatible binding ligand, a label comprising a detectable moiety and, optionally, a nucleic acid binding enhancer moiety.

According to yet another embodiment of the present invention, the aqueous solution further comprises one or more nucleic acid probes or primers complementary to the nucleic acid to be detected.

In accordance with another another aspect of the present invention, methods are provided for detecting the presence of a nucleotide sequence in nucleic acid of a sample using the aqueous solutions comprising a lipid or membrane fluidizing compound containing compositions of the present invention. Such methods are applicable to clinical specimens and are useful for diagnosing a variety of diseases and conditions.

In accordance with still yet another aspect of the present invention, kits are provided for releasing nucleic acid from a sample in a form suitable for directly detecting the nucleic acid. The kit comprises a vial containing an aqueous solution comprising one or more lipids for releasing nucleic acid from the cells and further comprising one or more of an enzyme(s) to degrade cell structure, a non-ionic membrane fluidizing compound(s) and a metal chelator(s). The aqueous solution is non-denaturing and non-inhibitory of enzymes or proteins used in nucleic acid release, amplification, labeling or detection.

In one embodiment, the kit further comprises or more nucleic acid probes or primers complementary to the nucleic acid to be detected, wherein said probes or primers are contained in the vial with the aqueous solution or are contained in one or more separate vials.

In another embodiment, the kit includes a means to prepare liposomes with the reagents supplied with the kit. In another embodiment, the kit further includes reagents for labeling nucleic acid, wherein said reagents are contained in the vial with the aqueous solution or are contained in one or more separate vials.

DETAILED DESCRIPTION OF THE INVENTION

The present invention provides novel compositions and methods for processing cell samples under conditions such that nucleic acids in cells or otherwise inaccessible to detection are released in a form suitable for direct nucleic acid detection assays. The compositions of the invention are designed to release nucleic acid from cells under conditions that do not result in denaturation of enzymes or proteins used in nucleic acid release, amplification, labeling or detection.

General Definitions:

Oligonucleotide: Low molecular weight deoxyribo-, ribo-, copolymers of deoxyribo- and ribonucleic acids of chain lengths between 3 and 150. Such oligonucleotides can have modified nucleotide residues such as—O—methoxy, phosphorothio-, methylphosphonates and others known in art.

Primers: Usually oligonucleotides which are used for extension reaction by a nucleic acid polymerase after a template primer hybrid is formed. Such primers can carry sequences specific for transcription by an RNA polymerase.

Nucleic Acid Probe: Nucleic acid with substantially complementary sequences to the target nucleic acids for detection or capture from a mixture. Such probes can be labeled for detection or immobilized onto a solid support to enrich the target by capture. A probe can be an single stranded or partially double stranded and can be an oligonucleotide or a larger nucleic acid.

Membrane fluidizing compound: A chemical substance that renders a cell membrane fluid or flexible to facilitate release of cellular material into solution or uptake of extracellular contents. Compounds that induce pinocytosis in addition to fluidizing the membrane also are included within the meaning of a membrane fluidizing compound as used herein. A membrane fluidizing compound can be a lipid or a non-lipid and can be ionic or non-ionic. Membrane fluidizing compounds generally do not cause cell death at lower concentrations that effect membrane fluidity, however, cell death typically results at higher concentrations of the compound.

Lipid: Any of various substances that are soluble in non-polar organic solvents (such as chloroform and ether), that with proteins and carbohydrates constitute the principal structural components of living cells, and that include fats, waxes, phosphatides, cerebrosides, and related and derived compounds.

Liposome vesicles: A vesicle composed of one or more concentric phospholipid bilayers. The structure of the liposomes may be as a multilamellar vesicle (MLV), a small unilamellar vesicle (SUV), a large unilamellar vesicle (LUV). A liposome is formed from a single lipid or combination of lipids (i.e., lipsosmal formulation) and optionally other compounds.

Thiocationic lipid: A lipid molecule with sulfur substitution and which is positively charged at neutral pH.

Photoreagent or photoactive reagents: Reagents which under appropriate wavelengths of light exposure form a covalent bond with nucleic acid.

Preferred Embodiments:

A composition of the present invention for releasing nucleic acid from a cell sample in a form suitable for directly detecting the nucleic acid comprises an aqueous solution comprising one or more lipids for releasing nucleic acid from the cells. As used herein, an aqueous solution is a water and/or other water miscible solvent and further includes a buffer to stabilize the pH between 4 and 11, with the ultimate pH depending on the stability of the nucleic acid to be released.

The aqueous solution comprising one or more lipids includes those lipids suitable for releasing cellular or otherwise inaccessible nucleic acid without denaturation. Liposomal formulations containing cationic lipids that have been used for delivery of oligonucleotides and other agents to target cells are useful for releasing nucleic acid from cells without denaturation as provided herein. PCT WO 96/40627 and U.S. Pat. Nos. 5,851,548, 5,759,519, 5,756,352, and 5,739,271 teach liposomal formulations containing cationic lipids.

The lipids used in the present compositions for releasing nucleic acid from cells include complex mixtures of different lipophilic substituents. Such complex mixtures allow for optimization of the physical properties of the liposomes, such as pH sensitivity, temperature sensitivity and size. For example, in certain embodiments, dioleoylphosphatidylethanolamine ("DOPE"), and other pH sensitive amphiphilic compounds can be used to formulate liposomes which destabilize at acidic pH. This promotes fusion of the liposome with endosomal membranes when exposed to the degradative acidic pH and enzymatic contents of the endosome, resulting in release of the contents of the endosome into the cytoplasm. (Ropert, et al., *Biochem. Biophys. Res. Comm.* 183(2):879–895 (1992); Juliano, et al., *Antisense Res.* and Dev. 2:165–176 (1992)). Although not wishing to be bound by any particular theory, it is believed that pH controlled degradation of liposomes in the cytoplasm of the cell enhances release of nucleic acids.

Lipids used in the present compositions for releasing nucleic acid from cells also can include sterols to enhance stability of liposomal vesicles both in vitro and in vivo. In particular, organic acid derivatives of sterols, such as cholesterol or vitamin $D_3$, which have been reported to be easier to formulate than their non-derivatized water-insoluble equivalents (U.S. Pat. Nos. 4,721,612 and 4,891,208), are useful in preparing liposomal formulations as described herein.

Preferred lipids for use in the present compositions and methods are cationic lipids (i.e., derivatives of glycerolipids with a positively charged ammonium or sulfonium ion-containing headgroup), including those useful in liposomal formulations for the intracellular delivery of negatively charged biomolecules such as oligonucleotides. The usefulness of cationic lipids may be derived from the ability of their positively charged headgroups to interact with negatively charged cell surfaces, although this is not known for certain. The cationic lipid N-(1-(2,3-dioleyloxy)propyl)-N, N, N-trimethylammonium chloride ("DOTMA") as described by Felgner, et al., *Proc. Natl. Acad. Sci.* (U.S.A) 84:7413–7417 (1987) (U.S. Pat. No. 4,897,355) is a cationic lipid with an ammonium group that can be used in liposomal formulations present in the compositions of the invention. In such formulations, DOTMA may bind to DNA through an ionic lipid-DNA complex that assists in releasing nucleic acid from a cell. Other ammonium ion-containing cationic lipid formulations that can be used in the nucleic acid releasing compositions of the present invention include the DOTMA analog, 1,2-bis(oleoyloxy)-3(trimethylammonio) propane ("DOTAP") (Stamatatos, et al., *Biochem.*, 27:3917–3925 (1988)); the lipophilic derivative of spermine (Behr, et al., *Proc. Natl. Acad. Sci.* (U.S.A), 86:6982–6986 (1989)); and cetyltrimethylammonium bromide (Pinnaduwage, et al., *Biochem. Biophys. Acta*, 985:33–37 (1989); Leventis, et al., *Biochem. Biophys. Acta*, 1023:124–132 (1990); Zhou, et al., *Biochem. Biophys. Acta*, 1065:8–14 (1991); Farhood, et al., *Biochem. Biophys. Acta*, 1111:239–246 (1992); and Gao, et al., *Biochem. Biophys. Res. Comm.*, 179:280–285 (1991)).

Cationic lipids are commercially available including DOTMA (Gibco BRL, Bethesda, Md.), DOTAP (Boehringer Mannheim, Germany), and 1,2-diacyl-3-trimethylammonium propane ("TAP") (Avanti Polar Lipids, Alabaster, AL).

Cationic lipids containing sulfonium ions (i.e., thiocationic lipids) also can be used in the present nucleic acid releasing compositions. Sulfonium ions have entirely different physical properties than ammonium ions, which provides sulfonium cationic lipids with some unique properties. Ammonium ion-containing compounds are classified as hard bases, because the nitrogen atom possesses high electronegativity, is difficult to polarize and oxidize, and the valence electrons are held tightly by the nucleus. This characteristic may account for some of the toxicity associated with ammonium ion-containing lipid formulations. In contrast, sulfonium ion-containing compounds are classified as soft bases, because the sulfur atom possesses low electronegativity, is easy to polarize and oxidize, and the valence electrons are held more loosely by the nucleus. This decreased charge density exhibited by sulfonium ion-containing (i.e. "thiocationic") lipids may effectuate an enhanced interaction with negatively charged cellular membranes, as well as a decreased toxicity, leading to compositions with increased ability to release cell nucleic acid in a non-denatured form.

Cationic lipids with relatively small polar headgroups as described by Feigner, et al., *J. Biol. Chem.*, 269(4):2550–2561 (1994), can be particularly useful in the present compositions for releasing nucleic acids. However, the sulfonium ion type cationic lipid, which has a relatively larger headgroup, also can be useful because of the physiochemical properties associated with the sulfonium ion. A lipid headgroup that consists of a sulfur atom surrounded by adjoining saturated carbon atoms exhibits a diffusion of charge to the neighboring carbon atoms that can facilitate interaction of the lipid with cellular membranes, as well as decrease the toxicity of the lipid (U.S. Pat. No. 5,759,519).

Liposomal preparations of the present invention can have a positively charged surface by including in the formulation, saturated or unsaturated aliphatic amines, including, for example, stearylamine and oleylamine, sphingosine, phosphatidylethanolamine, N-(1-(2,3-dioleyloxy)propyl)-N,N,N-trimethylammoniumchloride, cholesterylhemisuccinate, 3B-(N-(N',N'-dimethylaminoethane)carbamoyl)cholesterol and cholesterol(4'-trimethylammonio)butanoate, with preference given to stearylamine and sphingosine as described in U.S. Pat. No. 5,759,519.

The present compositions for releasing nucleic acid include a lipid that can form liposomes or other structures under the appropriate conditions. Prior methods of forming liposomes and encapsulating aqueous solution are applicable for preparing the nucleic acid releasing compositions of the present invention (e.g., Olson, et al., *Biophys, acta*, 557:9 (1979)). For example, prior art liposomal formulations used to encapsulate hemoglobin (e.g., U.S. Pat. No. 4,911,929) are to produce liposomal vesicles as described herein. Such liposomal formulation contains roughly equivalent quantities of cholesterol and phosphatidylcholine, with 5 to 10% negatively charged lipid, such as phosphatidic acid, dicetyl phosphate, or dimyristoyl phosphatidyl glycerol (DMPG). Hydration of the dried lipid film results in formation of multilamellar vesicles (MLV), which can be extruded at low-pressure (e.g., 50–90 psi) through filters of progressively smaller pore size to large unilamellar vesicles (LUVs). Once the liposomal vesicles are formed, any unencapsulated aqueous solution can be removed, if desired, by centrifugation or diafiltration and then recycled.

Lipid used for the formation of the liposome can be natural or synthetic and include phospholipids, glycolipids, and lipid related compounds. Exemplary lipids include, lecithin (phosphatidylcholine), phosphatidylethanolamine, phosphatidic acid, phosphatidylserine, phosphatidylinositol, phosphatidylglycerol, sphingomyelin, cardiolipin, and hydrogenated derivatives thereof, which can be used either alone or in combination. The glycolipids include cerebroside, sulfolipid (e.g., sulfatide), and ganglioside. The structure of the liposomes may be as a multilamellar vesicle (MLV), a small unilamellar vesicle (SUV), or large unilamellar vesicle (LUV).

To stabilize the lipid, an antioxidant such as tocopherol (vitamin E) can be added to the solution. A suitable amount of an antioxidant is about 0.01 to 0.5% by weight based on the weight of the phospholipid. The liposome composition of the invention also can contain as a stabilizer, a high molecular weight polymer such as albumin, dextran, vinyl polymers, non-ionic surface active agents, gelatin, and hydroxyethyl starch.

Liposomal vesicles that encapsulate aqueous solutions as used herein can be prepared by a variety of known methods. For example, conventionally used hydration, reversed phase evaporation, removal of surfactant, solvent injection, freeze-thawing and dehydration-rehydration can be employed.

In the hydration method, the selected lipids are dissolved in an organic solvent (e.g., chloroform and ether), which is non-denaturing, and the solvent is evaporated from the resulting solution yield a thin homogeneous film. The aqueous solution containing, for example, an enzyme(s), a non-ionic membrane fluidizing compound(s), a metal chelator(s) or nucleic acid probes or primers (discussed further below) is added to the thin membrane, and the mixture is subjected to agitation and sonication to yield a liposome preparation encapsulating the aqueous solution. The aqueous solution contains a buffer at a pH between 4 and 11. The pH of the buffer is chosen such that when the lipids or liposomes are added to an assay medium, the final pH in a range suitable to preserve nucleic acids in solution.

In the reversed-phase evaporation method, the selected lipids are dissolved in an organic solvent (e.g., chloroform and ether), as discussed above, and are added to the aqueous solution and subjected to agitation, sonication and high pressure homogenization to uniformly disperse the aqueous solution. The solvent is evaporated from this dispersion to yield a liposome preparation encapsulating the aqueous solution.

In the removal of surfactant approach, the selected lipids dissolved in organic solvent are mixed with a surfactant (e.g., cationic surfactant such as cholic acid or deoxycholic acid, and a non-ionic surfactant such as Triton X-100 and octyl-D-glucoside) and added to the aqueous solution, which is followed by agitation, sonication and high pressure homogenization to uniformly disperse the aqueous solution.

The surfactant is then removed by dialysis, gel filtration and ultrafiltration, which are applied singly or in combination.

In the solvent injection, approach, the selected lipids are dissolved in organic solvent and are added to the aqueous solution, which has been set for a temperature about 10° C. higher than the boiling point of the organic solvent. Then, the organic solvent is evaporated.

The aqueous solution of the present nucleic acid releasing compositions also can include, for example, substances other than lipids that enhance release of nucleic acid depending on the nature of the sample and the environment in which the nucleic acid is contained (e.g., the type of cell). Such nucleic acid releasing substances include, for example, an enzyme(s) to degrade cell structure, a non-ionic membrane fluidizing compound(s), and/or a metal chelator(s).

Enzymes suitable for use with lipid containing aqueous solution are available from natural sources or produced by recombinant DNA methods. Such enzymes include, for example, lysozyme, lipases, and proteinases such as proteinase K, pronase, trypsin and chymotrypsin. Lysozymes from bovine, chicken, human and lipases from wheat germ, human, yeast and other sources also are suitable enzymes to degrade cell structure. These enzymes preferably are nuclease free to support stability of released nucleic acids in solution. The aqueous solution containing lipids and enzymes for releasing nucleic acid can be encapsulated into a liposome, if desired.

The enzymes are used at a molar ratio of lipid to enzyme of between 10,000:1 and 1:10,000. The optimal ratio of enzyme to lipid can be readily determined by one skilled in the art. This can be accomplished by mixing target cells with various lipid:enzyme ratios, and determining the effectiveness of releasing nucleic acid in a probe hybridization assay.

Non-ionic membrane fluidizing compounds, which have been described in Suciu et al., *Mol. Microbiol.*, 21:181–95 (1996), Nabekura et al., *Pharm Res.*, 13(7):1069–72 (1996), and Lindow et al., Cryobiol., 32(3):247–258 (1995), and include aromatic alcohols such as all phenyl, napthyl, and higher alcohols, also can be used to release nucleic acid from cells without denaturation of enzymes or proteins. The hydrocarbon side chains of aromatic alcohols can be from $C_1$ to $C_{50}$ and longer, preferably between $C_1$ and $C_{20}$. The—OH residue can be at the $C_n$ terminus carbon for a primary alcohol or any place as in a secondary or tertiary alcohol. The C—C bonds in $C_n$ chain in addition to single bond can have unsaturated linkages in the form of double or triple bonds. The carbon chain also can have secondary and tertiary C-linkages. Phenethyl alcohol, sec-phenethyl alcohol, benzyl alcohol are examples of non-ionic membrane fluidizing compounds.

Non-ionic membrane fluidizing compounds can be included in the aqueous solutions of the present invention provided they enhance release of nucleic acids from cells without creating an enzyme or protein inhibitory environment. Such compounds can be present in the aqueous solution at a concentration between 0.001% and 10.0%. The final concentration of non-ionic membrane fluidizing compound in a sample for releasing nucleic acid is preferably between about 0.001 and 10% (v/v), more preferably between 0.01% and 5%, most preferably between 0.1 % and 2%. The ultimate concentration of the non-ionic membrane fluidizing compound depends on the nature of the fluidizing compound and the other components of the nucleic acid releasing composition. One skilled in the art can readily determine the proper concentration of membrane fluidizing compound for effective release of nucleic acid from a particular sample by determining binding of a specific probe to nucleic acid released by a particular formulation.

Most non-ionic membrane fluidizing compounds are more soluble in non-aqueous solvents. In such cases, stock solutions can be made in a solvent that is less polar than water, for example, in ethanol or isopropanol.

The aqueous solution of the nucleic acid releasing composition also can include metal chelators such as ethylenediaminetetraacetic acid (EDTA) and ethyleneguaninetetraacetic acid (EGTA). In addition, the aqueous solution can be heated to enhance release of the nucleic acid essentially as described in U.S. Pat. No. 5,837,452 (1988).

The compositions of the present invention are useful for releasing nucleic acid in a non-denatured form suitable for detection of a specific nucleotide sequence. Thus, it is preferred that the nucleic acid releasing compositions be non-denaturing and non-inhibitory of enzymes or proteins used in nucleic acid release, amplification, labeling or detection. This allows the composition to include a labeled or unlabeled nucleic acid probe or primer or other reagents useful in detection of a nucleotide sequence without additional steps to dilute the sample or neutralize denaturing conditions.

In some embodiments, the compositions for releasing nucleic acid also include reagents to label the released nucleic acid for later detection of formed hybrids. Such reagents for labeling nucleic acid comprise a binding ligand comprising a chemical moiety that binds to a nucleic acid and that, when activated by light (i.e., photochemistry), forms at least one covalent bond therewith, a label comprising a detectable moiety and optionally, a binding enhancer comprising a chemical moiety that has a specific affinity for nucleic acids (U.S. patent application Ser. No. 09/265,127).

The photochemical method provides more favorable reaction conditions than the usual chemical coupling method for biochemically sensitive substances. The DNA binding ligand and label can first be coupled and then photoreacted with the nucleic acid, or the nucleic acid can first be photoreacted with the binding ligand and then coupled to the label.

DNA-binding ligands useful herein for linking the nucleic acid component to the label can be any suitable photoreactive form of known DNA-binding ligand. Particularly preferred DNA-binding ligands are intercalator compounds such as the furocoumarins, e.g., angelicin (isopsoralen) or psoralen or derivatives thereof, which photochemically react with nucleic acids, e.g., 4'-aminomethyl-4,5'-dimethylangelicin, 4'-aminomethyl-trioxsalen (4'aminomethyl-4,5',8-trimethyl-psoralen), 3-carboxy-5- or -8-amino- or -hydroxy-psoralen, as well as mono- or bis-azido aminoalkyl methidium or ethidium compounds.

Particularly useful photoreactive forms of intercalating agents are the azidointercalators. Their reactive nitrenes are readily generated at long wavelength ultraviolet or visible light and the nitrenes of arylazides prefer insertion reactions over their rearrangement products (White, et al., *Meth. Enzymol.*, 46:644 (1977)). Representative intercalating agents include azidoacridine, ethidium monoazide, ethidium diazide, ethidium dimer azide (Mitchell, et al., *J. Am. Chem. Soc.*, 104:4265 (1982)), 4-azido-7-chloroquinoline, and 2-azidofluorene. A specific nucleic acid binding azido compound has been described by Forster, et al., *Nucleic Acid Res.*, 13:745 (1985). Other useful photoreactable intercalators are the furocoumarins which form (2+2) cycloadducts with pyrimidine residues. Alkylating agents also can be used as the DNA binding ligand, including, for example, bischloroethylamines and epoxides or aziridines, e.g., aflatoxins, polycyclic hydrocarbon epoxides, mitomycin and norphillin A.

DNA-binding ligands which do not inhibit nucleic acid amplification enzymes under amplification reaction conditions include, for example, 4'Biotinyl-PEG-4,5'-dimethylangelicin ("BPA"), Angelicin-DAPI-Biotin ("BDA"), Angelicin-bisbenzimidazole-PEG-azidonitrobenzene ("AZPIMA"), Angelicin-bisbenzimidazole-PEG-acridine ("APIMA"), Angelicinbisbenzimidazole-PEG-biotin ("BPIMA") and compounds described in U.S. Pat. Nos. 4,950,744 and 5,026,840. In such compounds, PEG represents any of the known forms of polyethyleneglycol, including pentaoxaheptadecane.

Usually, a stock solution of these compounds is prepared such that an aliquot of the stock solution is added to the reaction mixture to the desired final concentration. The desired concentration can be determined by one skilled in the art using known methods. Such methods include binding studies of the ligand with nucleic acids in a mock clinical sample. The concentration of the labeling reagent in the mixture should be between about 0.001 nanomolar and 10.0 millimolar, preferably between about 0.1 micromolar and 100 micromolar, and most preferably between about 0.1 micromolar and 10 micromolar. The DNA-binding ligand will be present in the aqueous solution of the present invention either as a mixture or as a component of a liposomal formulation.

The label, which is linked to the nucleic acid through the DNA-binding ligand, can be any chemical group or residue having a detectable physical or chemical property, i.e., labeling can be conducted by chemical reaction or physical adsorption. The label includes a functional chemical group to enable it to be chemically linked to the DNA binding ligand. Such labeling materials have been well developed in the field of immunoassays and, in general, most any label useful in such methods can be applied to label DNA as described herein.

Particularly useful labels are enzymatically active groups such as enzymes (Clin. Chem., 22:1243 (1976)), enzyme substrates (British Pat. No. 1,548,741), coenzymes (U.S. Pat. Nos. 4,230,797 and 4,238,565) and enzyme inhibitors (U.S. Pat. No. 4,134,792; fluorescers (Clin. Chem., 25:353 (1979)), and chromophores including phycobiliproteins; luminescers such as chemiluminescers and bioluminescers (Clin. Chem., 25:512 (1979) and ibid, 1531); specifically bindable ligands, i.e., protein binding ligands; antigens; and residues comprising radioisotopes such as $^3H$, $^{35}S$, $^{32}P$, $^{125}I$, and $^{14}C$. Such labels are detected on the basis of their own physical properties (e.g., fluorescers, chromophores and radioisotopes) or their reactive or binding properties (e.g., enzymes, substrates, coenzymes and inhibitors).

For example, a cofactor-labeled nucleic acid can be detected by adding the enzyme for which the label is a cofactor and a substrate for the enzyme. A hapten or ligand (e.g., biotin) labeled nucleic acid can be detected by adding an antibody or an antibody pigment to the hapten or a protein that binds the ligand (e.g., avidin), tagged with a detectable molecule. A detectable molecule has a measurable physical property (e.g, fluorescence or absorbence) or is participant in an enzyme reaction (e.g., see above list). For example, one can use an enzyme which acts upon a substrate to generate a product with a measurable physical property. Examples of the latter include, but are not limited to, betagalactosidase, alkaline phosphatase, papain and peroxidase. For in situ hybridization studies, the final product of the substrate is preferably water insoluble. Other labels, e.g., dyes, will be evident to one having ordinary skill in the art.

If the label is an enzyme, the labeled DNA is ultimately placed in a suitable medium to determine the extent of catalysis. Thus, if the enzyme is a phosphatase, the medium can contain nitrophenyl phosphate and one can monitor the amount of nitrophenol generated by observing the color. If the enzyme is a beta-galactosidase, the medium can contain o-nitro-phenyl-D-galacto-pyranoside, which also liberates nitrophenol. The label can be linked to the DNA binding ligand, e.g., acridine dyes, phenanthridines, phenazines, furocoumarins, phenothiazines and quinolines, by direct chemical linkage such as involving covalent bonds, or by indirect linkage such as by the incorporation of the label in a microcapsule or liposome, which in turn is linked to the binding ligand. Methods by which the label is linked to a DNA binding ligand such as an intercalator compound are well known in the art and any convenient method can be used.

Advantageously, the DNA binding ligand is first combined with label chemically and thereafter combined with the nucleic acid component. For example, since biotin carries a carboxyl group, it can be combined with a furocoumarin by way of amide or ester formation without interfering with the photochemical reactivity of the furocoumarin or the biological activity of the biotin. Aminomethylangelicin, psoralen and phenanthridium derivatives can similarly be linked to a label, as can phenanthridium halides and derivatives thereof such as aminopropyl methidium chloride (Hertzberg et al, *J. Amer. Chem. Soc.*, 104:313 (1982)). Alternatively, a bifunctional reagent such as dithiobis succinimidyl propionate or 1,4-butanediol diglycidyl ether can be used directly to couple the DNA binding ligand to the label where the reactants have alkyl amino residues, again in a known manner with regard to solvents, proportions and reaction conditions. Certain bifunctional reagents, possibly glutaraldehyde may not be suitable because, while they couple, they may modify nucleic acid and thus interfere with the assay. Routine precautions can be taken to prevent such difficulties.

The particular sequence used in making the labeled nucleic acid can be varied. Thus, for example, an amino-substituted psoralen can first be photochemically coupled with a nucleic acid, the product having pendant amino groups by which it can be coupled to the label, i.e., labeling is carried out by photochemically reacting a DNA binding ligand with the nucleic acid in the test sample. Alternatively, the psoralen can first be coupled to a label such as an enzyme and then to the nucleic acid.

Advantageously, the DNA binding ligand can be linked to the label by a spacer, which includes a chain of up to about 40 atoms, preferably about 2 to 20 atoms, selected from the group consisting of carbon, oxygen, nitrogen and sulfur. Such spacer can be the polyfunctional radical of a member selected from the group consisting of peptide, hydrocarbon, polyalcohol, polyether, polyamine, polyimine and carbohydrate, e.g., -glycyl-glycyl-glycyl- or other oligopeptide, carbonyl dipeptides, and omega-amino-alkane-carbonyl radical or the like. Sugar, polyethylene oxide radicals, glyceryl, pentaerythritol, and like radicals also can serve as spacers. Spacers can be directly linked to the nucleic acid-binding ligand and/or the label, or the linkages may include a divalent radical of a coupler such as dithiobis succinimidyl propionate, 1,4-butanediol diglycidyl ether, a diisocyanate, carbodiimide, glyoxal, glutaraldehyde, or the like.

Nucleic acid labeling reagents including the binding ligand and label also optionally can include a binding enhancer as described U.S. application Ser. No. 09/265,127. Covalent or non-covalent complexes of a binding ligand, a binding enhancer and a label is referred to herein as a "LAC."

The nucleic acid binding enhancer ("binding enhancer"), serves to enhance the affinity of the LAC for nucleic acids above that exhibited with the binding ligand alone. Accordingly, binding enhancers tend to have a specific affinity for nucleic acids when compared to non-nucleic acid sample/reaction constituents. The binding enhancer can be the same as or different from the binding ligand. In other words, the binding ligand and the binding enhancer can each be an intercalator, wherein one of the two is a monoadduct-forming species, and the other is present to enhance binding by this monoadduct-forming species. Examples of such "dual role" binding ligands are described in Chaires, et al., *J. Med. Chem.*, 40:261–266 (1977). Therein, it has been described that binding of a bis-intercalating anthracycline antibiotic reached as high as $10^{11}$ at 20° C. It was also shown that the affinity of a similar monointercalator is not above $10^7$ (Chaires, et al., *Biochem.*, 35:2047–2053 (1996)).

The binding enhancer also can be a non-intercalating compound. There are many non-intercalating nucleic acid binding molecules known in the art. A bis-benzimidazole derivative commonly known as Hoechst 33258 has shown affinity as high as $3.2 \times 10^8 M^{-1}$(Haq, et al., *J. Mol. Biol.*, 271:244–257 (1997)). Other non-intercalating binding enhancers are oligo pyrroles, phenyl indole derivatives and the like. These molecules do not bind nucleic acids solely on the basis of positive charge. Other suitable binding enhancers bind nucleic acids on the basis of hydrogen bond formation, hydrophobic interaction in the major or minor groove of the nucleic acid double helix and other non-ionic interactions that give rise to high affinity reactions with nucleic acids.

Not every compound capable of forming an electrostatic bond with a negatively charged nucleic acid can serve as a binding enhancer. For example, polycations such as polyamines are generally not suitable for use in the present invention because of their inability to specifically bind to nucleic acids in crude samples and in the presence of amplification reaction components. Such positively charged compounds can, for example, non-specifically bind to all anionic macromolecules present in the sample, and not just to nucleic acids. In addition, the binding enhancer should be capable of specifically binding to nucleic acids in the presence of 10 to 20 mM magnesium, which is typically required for most amplification reactions. At this concentration, compounds that bind to nucleic acids solely on the basis of electrostatic interactions do not form stable complexes with nucleic acids and thus require a greater concentration of LAC for efficient labeling.

As discussed above, the binding ligand for labeling nucleic acid is either directly or indirectly linked to a label. Such attachment can be either covalent or ionic, so long as it is stable under the conditions in which the LAC is employed. Chemical attachments can be accomplished by any of a variety of well known methods. For example, if the binding ligand contains or is derivatised to contain an available carboxyl group and the label contains or is derivatized to contain an available amino group, the two can be reacted together to form an ester linkage. By "available", it is meant that the formation of a linkage will not interfere with the functioning of the label (i.e., its ability to be detected or to catalyze a detectable reaction) or the ligand (i.e., it's ability to bind nucleic acids). Particularly useful labels are enzymes, enzyme substrates, fluorophore, radioisotopic compounds, chromophores, magnetically responsive compounds, antibody epitope-containing compounds, haptens, and the like.

The binding ligand, binding enhancer, and label or labeling nucleic acid can also be indirectly attached via a linker. Such linkers are specifically designed to promote efficient binding of the binding ligand to the nucleic acids and functioning of the label attached thereto. This occurs by providing adequate physical separation between the two components of the LAC to prevent interference of one by the other. The use of linkers is described generally in U.S. Pat. Nos. 4,582,789 and 5,026,840. Certain compounds can serve the dual role of a binding enhancer and a linker. For example, linkers can be constructed from positively charged compounds, such that they enhance binding with negatively charged nucleic acids. However, in order for the linker to also serve as a binding enhancer, it is necessary for it to have a specific affinity for nucleic acids, and not just a structure specific electrostatic affinity for negatively charged compounds. The polyalkylamine linkers described in U.S. Pat. No. 5,026,840 are not optimal as binding enhancers but are suitable as linkers.

In a preferred embodiment, a bifunctional linker is used that is capable of reacting with both the nucleic acid binding moiety and the label to form a chemical bridge therebetween. However, in an alternate embodiment, a multifunctional linker can be employed, to which the binding ligand, the binding enhancer and the label are attached as a "branched" complex. Such complex formats and chemical reactions for forming these types of complexes are well known in the art.

Compositions comprising an aqueous solution for releasing nucleic acid of the present invention having the appropriate combination of nucleic acid releasing, labeling and detecting reagents to achieve single step processing and detection also are provided herein. Such compositions require that all the components of the composition not be denaturing or inhibitory to enzymes or proteins used in nucleic acid release, amplification, labeling or detection. All these components when mixed to produce the final reagent are delivered to the sample in an aqueous solution which can be water or a buffer solution pH of which is preferably between 3 and 12. More preferably between 5 and 10 such that the released nucleic acids are not substantially degraded. The particular reagents to be added and their optimal concentration depends on various factors including the nature of the sample and the particular reagents chosen. One skilled in the art can readily select the proper reagents and determine an optimal concentration of each without resort to undue experimentation.

The present invention also provides methods and kits for using the disclosed compositions in assays for detecting the presence of a nucleotide sequence in nucleic acid of a sample containing cells. Such assays are used for diagnosis of infectious diseases, cancer, human genetic disorders, and others like histocompatibility (e.g., HLA) typing, forensic and paternity testing. For example, by contacting and treating the sample with the above described compositions that contain reagents for releasing nucleic acid from cells and appropriate labeling reagents (e.g., LACs), the samples can be used for hybridization diagnosis without any further processing of the sample. Thus, a urine sample, for instance, that is suspected of bacterial infections can be labeled without centrifugation, filtration or dialysis and the cells in the samples are lysed without any separation step.

Test samples include body fluids, e.g., urine, blood, semen, cerebrospinal fluid, pus, amniotic fluid, tears, or semisolid or fluid discharge, e.g., sputum, saliva, lung aspirate, vaginal or urethral discharge, stool or solid tissue samples, such as a biopsy or chorionic villi specimens. Test samples also include samples collected with swabs from the skin, genitalia, or throat. The compositions of the invention can be added directly to the sample or to cells isolated from the sample.

The assay method can detect the nucleic acid from essentially any species of organism, including, for example, Acintobacter, Actinomyces, Aerococcus, Aeromonas, Alclaigenes, Bacillus, Bacteriodes, Bordetella, Branhamella, Bevibacterium, Campylobacter, Candida, Capnocytophagia, Chlamydia, Chromobacterium, Clostridium, Corynebacterium, Cryptococcus, Deinococcus, Enterococcus, Erysielothrix, Escherichia, Flavobacterium, Gemella, Gonorrhea, Haemophilus, Klebsiella, Lactobacillus, Lactococcus, Legionella, Leuconostoc, Listeria, Micrococcus, Mycobacterium, Neisseria, Nocardia, Oerskovia, Paracoccus, Pediococcus, Peptostreptococcus, Propionibacterium, Proteus, Psuedomonas, Rahnella, Rhodococcus, Rhodospirillium, Staphlococcus, Streptomyces, Streptococcus, Vibrio, and Yersinia. Also included are viruses such as the hepatitis viruses and human immunodeficiency viruses (HIV).

The present methods also can be used to detect nucleic acid from eukaroytes (protists) in samples from higher organisrns, such as animals or humans. Eukaroytes include algae, protozoa, fungi and slime molds. The term "algae" refers in general to chlorophyll-containing protists, descriptions of which are found in Smith, *Cryptogamic Botany*, 2nd ed. Vol. 1, Algae and Fungi, McGraw-Hill, (1955). Eukaryotic sequences according to the present invention includes all disease sequences. Accordingly, the detection of genetic diseases, for example, also are embraced by the present invention.

Methods of detecting a nucleotide sequence involve contacting the above described aqueous compositions for releasing nucleic acid with a sample suspected of containing the nucleotide sequence of interest. The mixture is incubated for an appropriate period of time and under conditions suitable for releasing the nucleic acid from the cells. If release and detection of the nucleic acid is sought as a single step, the nucleic acid releasing composition also includes one or more nucleic acid probes or primers that are complementary to the nucleotide sequence to be detected and other reagents depending on the detection format to be used. Such nucleic acid primers or probes can be an oligonucleotide or, in some cases, a larger nucleic acid molecule.

If the sample already contains released or isolated nucleic acid, the incubation period can be between a few seconds to five min. When the sample contains whole cells, incubation between two minutes (min) to two hours ("hrs") may be necessary.

Amplification methods suitable for use with the present methods include, for example, polymerase chain reaction (PCR), ligase chain reaction (LCR), transcription mediated amplification (TMA) reaction, nucleic acid sequence based amplification (NASBA) reaction, and strand displacement amplification (SDA) reaction. These methods of amplification are well known in the art.

PCR can be performed as according to Whelan, et al, *J. Clin. Microbiol.*, 33(3):556–561 *(1995). Briefly, a PCR reaction mixture includes two specific primers, dNTP, 0.25 Units (U) of Taq polymerase, and 1×PCR Buffer. For every 25 µl PCR reaction, a 2 µl sample (e.g., isolated DNA from target organism) is added and amplified on a thermal cycler. The amplification cycle includes an initial denaturation, and up to 50 cycles of annealing, strand elongation and strand separation (denaturation).

LCR can be performed as according to Moore, et al., *J. Clin. Microbiol.*, 36(4):1028–1031 (1998). Briefly, an LCR reaction mixture contains two pair of probes, dNTP, DNA ligase and DNA polymerase representing about 90 µl, to which is added 100 µl of isolated nucleic acid from the target organism. Amplification is performed in a thermal cycler (e.g., LCx® thermal cycler, Abbott Labs, North Chicago, Ill.).

SDA can be performed as according to Walker, et al., *Nucleic Acids Res.*, 20(7):1691–1696 (1992). Briefly, an SDA reaction mixture contains four SDA primers, dGTP, dCTP, TTP, dATPS, 150 U of Hinc II, and 5 U of exonuclease deficient *E. coli* DNA polymerase I. The sample mixture is heated 95° C. for 4 min to denature target DNA prior to addition of the enzymes. After addition of the two enzymes, amplification is carried out for 120 min. at 37° C. in a total volume of 50 µl. The reaction is terminated by heating for 2 min at 95° C.

NASBA can be performed as according to Heim, et al., *Nucleic Acids Res.*, 26(9):2250–2251 (1998). Briefly, an NASBA reaction mixture contains two specific primers, dNTP, NTP, 6.4 U of AMV reverse transcriptase, 0.08 U of Escherichia coli Rnase H, and 32 U of T7 RNA polymerase. The amplification is carried out for 120 min at 41° C. in a total volume of 20 µl.

TMA can be performed as according to Wylie, et al., *Journal of Clinical Microbiology*, 36(12):3488–3491 (1998). In TMA, nucleic acid targets are captured with magnetic beads containing specific capture primers. The beads with captured targets are washed and pelleted before adding amplification reagents, which contain amplification primers, dNTP, NTP, 2500 U of reverse transcriptase and 2500 U of T7 RNA polymerase. A 100 µl TMA reaction mixture is placed in a tube, 200 µl oil reagent is added and amplification is accomplished by incubation at 42° C. in a waterbath for one hour ("hr").

A variety of amplification enzymes are well known in the art and include, for example, DNA polymerase, RNA polymerase, reverse transcriptase, Q-beta replicase, thermostable DNA and RNA polymerases. Because these and other amplification reactions are catalyzed by enzymes, it is important for a single step assay that the nucleic acid releasing reagents and the detection reagents are not potential inhibitors of amplification enzymes if the ultimate detection is to be amplification based.

Also included in the composition for amplification are appropriate nucleoside triphosphates, amplification buffer and certain ions. The concentrations of nucleic acid primers and enzymes can be selected for specific use. For example, for polymerase chain reaction, the concentration of the nucleic acid primer is between 1 picomole and 1 millimole when added to the sample. The enzyme concentration can vary between about 0.01 U and 100,000U. One skilled in the art can determine the optimal concentration of enzyme and other reagents by routine experimentation.

Detection of the nucleotide sequences also can be performed directly without amplification by hybridizing the sample nucleic acid to the nucleic acid probe present in the composition. In this case, the nucleic acid is contacted and incubated with the labeling reagents (provided in the nucleic acid release composition or separately) and the mixture is irradiated at a particular wavelength for the covalent interaction between the photochemically reactive DNA binding ligand and the test sample to take place. After labeling, the material is hybridized under specified hybridization conditions with a probe specific for the target nucleic acid.

Hybridization of the labeled sample nucleic acid or the labeled nucleic acid probe can be detected in any conventional hybridization assay format and, in general, in any format suitable for detecting the hybridized product or aggregate comprising the labeled nucleic acid. If the sample nucleic acid has been labeled, it can be used for hybridization in solution and solid-phase formats, including, in the latter case, formats involving immobilization of either sample or nucleic acid probe. For example, preimmobilized nucleic acid probe can be hybridized with labeled sample nucleic acid. The presence of label associated with the solid phase indicates hybridization between the probe and the sample nucleic acid and, thus, detection of the target nucleotide sequence. Alternatively, unlabeled sample nucleic acid can be preimmobilized and a labeled probe evaluated for hybridization thereto.

Preferable concentration for the probe is between about 0.01 picomole and 10 millimoles, more preferably between about 1 picomole and 1 millimole, and most preferably between about 10 picomole and 10 micromoles. Methods of detecting hybrids on solid phases are well known in the art and have been extensively described (e.g., U.S. Pat. Nos. 5,232,831, 4,950,613, 486,539 and 4,563,419).

The nucleic acid probe comprises at least one hybridizable, e.g., singlestranded, base sequence substantially complementary to or homologous with the nucleotide sequence to be detected. However, such base sequence need not be a single continuous polynucleotide segment, but can comprise two or more individual segments interrupted by non-homologous sequences. These non-homologous sequences can be linear or they can be self-complementary and form hairpin loops. In addition, the homologous region of the probe can be flanked at the 3'- and 5' termini by non-homologous sequences, such as those comprising the DNA or RNA or a vector into which the homologous sequence had been inserted for propagation. In either instance, the probe as presented as an analytical reagent will exhibit detectable hybridization at one or more points with sample nucleic acids of interest. Linear or circular hybridizable, e.g., single-stranded polynucleotides can be used as the probe element, with major or minor portions being duplexed with a complementary polynucleotide strand or strands, provided that the critical homologous segment or segments are in single-stranded form and available for hybridization with sample DNA or RNA. Useful probes include linear or circular probes wherein the homologous probe sequence essentially is a single-stranded form (Hu et al., *Gene*, 17:271 (1982)).

The nucleic acid probe can be used in any conventional hybridization technique. As improvements are made and conceptually new formats are developed, such can be readily applied to the present probes. Conventional hybridization formats that are particularly useful include those wherein the sample nucleic acids or the polynucleotide probe are immobilized on a solid support (solid-phase hybridization) and those wherein the polynucleotide species are all in solution (solution hybridization).

In solid-phase hybridization formats, one of the polynucleotide species participating in hybridization is fixed in an appropriate manner in its singlestranded form to a solid support. Useful solid supports are well known in the art and include those, for example, which bind nucleic acids either covalently or non-covalently. Non-covalent binding supports, which are generally understood to involve hydrophobic bonding include naturally occurring and synthetic polymeric materials, such as nitrocellulose, derivatized nylon and fluorinated polyhydrocarbons, in a variety of forms such as filters, beads or solid sheets. Covalent binding supports (in the form of filters, beads or solid sheets, just to mention a few) are also useful and comprise materials having chemically reactive groups or groups such as dichlorotriazine, diazobenzyloxymethyl, and the like, which can be activated for binding to polynucleotides.

It well known that non-covalent immobilization of an oligonucleotide to a solid support such as nitrocellulose paper is generally ineffective for detecting hybridization. Thus, covalent immobilization is preferred and can be achieved by phosphorylation of an oligonucleotide by a polynucleotide kinase or by ligation of the 5'-phosphorylated oligonucleotide to produce multi-oligonucleotide molecules capable of immobilization. The conditions for kinase and ligation reaction have been described previously (e.g., Sambrook et al., *Molecular Cloning: A Laboratory Manual*, Cold Spring Harbor Laboratory, 1.53 and 5.33 (1989). Thus oligonucleotide probes specific for genetic defects related to hemoglobinopathies, such as sickle cell anemia and alpha-thalassemias can be immobilized on nitrocellulose paper and contacted with patient sample nucleic acid labeled by the above described method. The photochemical labeling can be done in a single step without the need to obtain purified nucleic acid samples and without affecting the specific hybridizability of the labeled sample.

A typical solid-phase hybridization technique begins with immobilization of sample nucleic acids onto the support in single-stranded form. This initial step essentially prevents reannealing of complementary strands from the sample and can be used for concentrating sample material on the support for enhanced delectability. The nucleic acid probe is then contacted with the support and hybridization detected by measurement of the label as described herein. The solid support provides a convenient means for separating labeled probe, which has hybridized to the sequence to be detected, from probe that has not hybridized.

Another method of interest is the sandwich hybridization technique wherein one of two mutually exclusive fragments of the homologous sequence of the probe is immobilized and the other is labeled. The presence of the polynucleotide sequence of interest results in dual hybridization to the immobilized and labeled probe segments (*G. Rankim*, et al., 21:77–85 (1983)).

In one embodiment, the immobile phase of the hybridization system can be a series or matrix of spots of known kinds and/or dilutions of denatured DNA. This can be prepared by pipetting appropriate small volumes of native DNA onto a dry nitrocellulose or nylon sheet, floating the sheet on a sodium hydroxide solution to denature the DNA, rinsing the sheet in a neutralizing solution, then baking the sheet to fix the DNA. Before DNA:DNA hybridization, the sheet is usually treated with a solution that inhibits non-specific binding of added DNA during hybridization.

In solid phase detection systems, unhybridized labeled test sample can be removed by washing following hybridization. After washing, the hybrid is detected through the label carried by the test sample, which is specifically hybridized with a specific probe.

The present invention further features kits that incorporates the components of the invention and makes possible convenient performance of the invention. Such kit may also include other materials that would make the invention a part of other procedures including adaptation to multi-well technologies. The items comprising the kit may be supplied in separate vials or may be mixed together, where appropriate.

EXAMPLES

Materials

The synthesis of several new lipids is described in Examples 1–3, other lipids DOPE (Avanti Polar Lipids); DODMECAP, DOMCATOP, DOMHYTOP, DODMECAP, OBEHYTOP and OBECATOP were prepared as described in PCT WO 96/40627.

The lipids and other materials used in the present invention include the materials described in WO 96/40627 and other commercially available materials. The synthesis of new compounds are described below. Unless indicated otherwise, parts are parts by weight, molecular weight is weight average molecular weight, temperature is in degrees Centigrade, and pressure is at or near atmospheric.

Example 1

Synthesis of 3-(2-Aminopropyl-1,3-dihexadecyloxypropyl) Hexadecyl Ether

This example describes the synthesis of a lipid compound useful for releasing nucleic acids from cells according to the methods and compositions of the invention. A three step procedure is provided as follows.

Step 1. Synthesis of 1,3-Dihexadecyloxy-2-aminopropane

A solution of 2-amino-1,3-propanediol (Serinol: Aldrich Chem. Co., Milwaukee, Wis.; Catalog No. 35,789-8) in tetrahydrofuran (THF) is added dropwise with vigorous stirring to a slurry of sodium hydride in THF over a period of 1–2 hrs. The reaction mixture is stirred for an additional 30 minutes to 1 hr at room temperature. Hexadecyl tosylate in THF is added dropwise to the mixture with vigorous stirring over a period of 1–1.5 hrs. The reaction mixture is stirred at room temperature for 1 hr and worked up by addition of isopropanol to destroy excess sodium hydride. The reaction mixture is extracted with chloroform (3×100 mL) and the combined chloroform layers are washed with water (2×50 mL), saturated NaCl (1×50 mL) and dried ($MgSO_4$). The dried chloroform layer is evaporated under vacuum to afford the product as an off-white solid.

Step 2. Synthesis of N-(3-Hydroxypropyl)-1,3-dihexadecyloxypropyl-2-amine

The compound from Step 1, above, is dissolved in methylene chloride and added to a solution of 3-bromopropanol in methylene chloride containing triethyl amine with vigorous stirring. The reaction mixture is stirred at room temperature for an additional 8–36 hrs. Upon completion of reaction, as shown by thin layer chromatography (TLC), the reaction mixture is extracted with methylene chloride. The methylene chloride layer is washed with dilute hydrochloric acid (3×50 mL), water (3×100 mL), saturated NaCl (1×75 mL) and dried ($MgSO_4$). The dried methylene chloride is evaporated under vacuum to afford the product as a solid.

Step 3. Synthesis of 3-(2-Aminopropyl-1,3-dihexadecyloxypropyl) Hexadecyl Ether

The compound from step 2, above, is dissolved in THF containing a trace of methylene chloride and is added dropwise with vigorous stirring to a suspension of sodium hydride in THF over a period of 45 minutes to 2 hrs. The reaction mixture is stirred for an additional 1 hr at room temperature. A solution of hexadecyl bromide (Aldrich Chem. Co., catalog No. 23,445-1) in THF is added dropwise with vigorous stirring over a period of 2 hrs. The reaction mixture is stirred for additional 2–4 hrs at room temperature. The reaction mixture is quenched by adding isopropanol and the mixture is worked up by extraction with methylene chloride. The methylene chloride layer is washed in water (3×100 mL), saturated NaCl (1×50 mL) and dried ($MgSO_4$). The dried organic layer is evaporated under vacuum to afford the product as a white solid.

Example 2

Synthesis of 3-(2Aminopropyl-1-octadecyloxy-3-benzyloxypropyl) Benzyl Sulfide.

This example describes the synthesis of a lipid compound useful for releasing nucleic acids according to the methods and compositions of the invention. A three step procedure is provided as follows.

Step 1. Synthesis of 1-Octadecyloxy-3-benzyloxy-2-aminopropane

A solution of 2-amino-1,3-propanediol in THF is added dropwise with vigorous stirring to a suspension of sodium hydride over a period of 45 minutes to 2 hrs. The reaction mixture is stirred at room temperature for an additional hr and sequentially treated with a solution of one equivalent each of octadecyl bromide and benzyl bromide, respectively. The reaction mixture is stirred at room temperature for 4–14 hrs. The reaction mixture is worked up by extraction with methylene chloride. The methylene chloride layer is washed with water (3×50 mL), saturated NaCl (1×50 mL) and dried ($MgSO_4$). The dried organic layer is evaporated under vacuum to afford the product as a white solid.

Step 2. Synthesis of 2-N-(3-mercaptopropyl)-amino-1-octadecyloxy-3-benzyloxypropane A solution of 1-octadecyloxy-3-benzyloxy-2-aminopropane from step 1, above, and 3-chloro-1-propanethiol (Aldrich, catalog No. C6,860-1) in methylene chloride containing diisopropylethyl amine is stirred at room temperature for 8–36 hrs. Upon completion of reaction, the reaction mixture is extracted with methylene chloride and washed with dilute acid. The organic layer is washed with water (3×75 mL), saturated NaCl (1×75 mL) and dried ($MgSO_4$). The dried organic layer is evaporated under vacuum to yield a white solid product.

Step 3. Synthesis of 3-(2-Aminopropyl-1-octadecyloxy-3-benzyloxypropyl) Benzyl Sulfide A solution of octadecyl bromide in methylene chloride is added dropwise with vigorous stirring to a solution of the compound from step 2, above, in methylene chloride containing triethyl amine over a period of 45 minutes to 2 hrs. The reaction mixture is stirred for an additional 2–4 hr at room temperature. The reaction mixture is poured into a mixture of ice-water and the mixture is worked up by extraction with methylene chloride. The methylene chloride layer is washed with water (3×100 mL), saturated NaCl (1×50 mL) and dried ($MgSO_4$). The dried organic layer is evaporated under vacuum to yield a white solid product.

Example 3

Synthesis of Bis(3-benzyloxypropyl-1-octadecyloxy-3-benzyloxy-2-propyl amine)-polyethyleneglycol.

The following two steps describe the synthesis of a lipid compound, bis(3-benzyloxypropyl-1-octadecyloxy-3-benzyloxy-2-propyl amine)pentaoxaheptadecane. This is one member of the class of compounds, bis(3-benzyloxypropyl-1-octadecyloxy-3-benzyloxy-2-propyl amine)-polyethyleneglycol (polyethyleneglycol: "PEG"), which is a conjugate of a membrane fluidizing compound and a lipid. This compound can be used instead of a simple lipid compound in releasing nucleic acid according to the methods and compositions of the invention.

Step 1. Synthesis of Pentaoxaheptadecane Ditosylate

A solution of p-toluenesufonyl chloride (74 g, 0.39 mol) is added dropwise to a stirred solution containing hexamethylene glycol (50 g, 0.18 mol) trimethylamine (40 g, 0.39 mol) in methylene chloride (400 mL) at 0° C. The reaction mixture is stirred for 1 hr at room temperature. The mixture is filtered and the filtrate is concentrated under vacuum in a rotary evaporator. The residue is suspended in ethylacetate (500 mL) and filtered. The filtrate concentrated under vacuum to afford yellow oil. The yellow oil is triturated with hexane and the resulting oil dried under vacuum to afford 108 g of yellow oil.

Step 2. Synthesis of Bis(3-benzyloxypropyl-1-octadecyloxy-3-benzyloxy2-propylamine)-PEG A solution containing the compound from Example 2, Step 2 and pentaoxaheptadecanoate ditosylate is combined in dimethylformamide containing diisopropylethyl amine and stirred at room temperature for 4–48 hrs. Upon completion of reaction as shown by TLC, the reaction mixture is poured over ice-water. The mixture is stirred for 1–2 hrs and extracted with methylene chloride. The organic layer is washed with dilute acid, water (3×50 mL), saturated NaCl (1×50 mL) and dried (MgSO$_4$). The dried methylene chloride is evaporated under reduced pressure to afford the product as a white solid.

Example 4

Preparation of Aqueous Solutions Formulated with Lipids for Releasing Nucleic Acids This example describes an aqueous solution containing lipids for releasing nucleic acid from cells. 80 micromoles of total lipid (which includes lipid, cholesterol or other sterol, and oleic acid alone or in combination with titratable amphiphile and sterol in 10:5:2 ratio) is dissolved in chloroform and dried. The dried lipid is rehydrated with 1 mL of an aqueous solution of the reagents to be mixed or formulated. Rehydration is performed by vortexing the mixture overnight at 37° Centigrade ("C"). For liposomal preparations, the mixture is further processed by freeze thawing and extruded through polycarbonate filters and further purified by gel filtration. The formulations can be prepared in presence of a reversible amplification inhibitor. Such inhibitors are added when the mixture also contains reagents for an amplification reaction.

Example 5

Preparation of Aqueous Solutions Formulated with Lipids and Enzymes

This example describes a method for preparing aqueous lipid solutions containing enzymes that are useful for releasing nucleic acid according to the methods and compositions of the invention. The following aqueous lipid containing solutions are prepared:

Reagent A:
  80 μl dried lipid (Example 4) and 1 mL of 50 mM Sodium Acetate (pH 6) containing 100,000 units of lysozyme (Sigma Chemical Co., St. Louis, Mo.).
Reagent B:
  80 μl dried lipid (Example 4) and 1 mL of 10 mM Borate (pH 8) containing 100,000 units of lipase (Sigma Chem. Co.).
Reagent C:
  80 μl dried lipid (Example 4) and 1 mL of 10 mM Borate (pH 8) containing 1 mg proteinase K (Sigma Chem. Co.).
Reagent D:
  80 μl dried lipid (Example 4) and 1 mL of 50 mM Sodium Acetate (pH 6) containing 50,000 units each of lysozyme and lipase.

Rehydration is carried out by vortexing the mixture overnight at 37° C. For liposomes, the mixture is further processed by freeze thawing and extrusion through polycarbonate filters (0.1 μM pore). The formulations can be prepared in presence of a reversible amplification inhibitor. Such inhibitors are used only when the mixture is prepared for an amplification reaction.

Example 6

Preparation of Aqueous Solutions Formulated with Lipids and Enzymes and a Probe

This example describes the preparation of aqueous lipid solutions containing enzymes and a probe that are useful for releasing nucleic acid and hybridizing the nucleic acid to the probe. The following aqueous lipid containing solutions are prepared:

The reagent solution to be mixed or formulated contains an oligonucleotide probe for subsequent hybridization. The reagents include:

Reagent A:
  80 μl dried lipid (Example 4) and 1 mL of 50 mM Sodium Acetate (pH 6) containing 100,000 units of lysozyme (Sigma Chem. Co.) and 1 micromolar of the probe.
Reagent B:
  80 μl dried lipid (Example 4) and 1 mL of 10 mM Borate (pH 8) containing 100,000 units of lipase (Sigma Chem. Co.) and 1 micromolar of the probe.
Reagent C:
  80 μl dried lipid (Example 5) and 1 mL of 10 mM Borate (pH 8) containing 1 mg of proteinase K (Sigma Chem. Co.), 1 mM EDTA and 1 micromolar of the probe.
Reagent D:
  80 μl dried lipid (Example 4) and 1 mL of 50 mM Sodium Acetate (pH 6) containing 50,000 units each of lysozyme and lipase, and 1 micromolar of the probe.

Rehydration is carried out by vortexing the mixture overnight at 37° C. For liposomes, the mixture is further processed by freeze thawing and extruded through polycarbonate filters and further purified by gel filtration. The formulations can be prepared in presence of a reversible amplification inhibitor. Such inhibitors are used only when the mixture is prepared for an amplification reaction.

Example 7

Preparation of Aqueous Solutions for Releasing and Labeling Nucleic Acid

This example describes the preparation of aqueous solutions containing lipids and other compounds for releasing and labeling nucleic acid.

Aqueous solutions containing lipids and formulated with enzymes and other substances as described in Examples 4, 5 and 6 are combined with a photoreative DNA binding ligand, such as BPA (Example 17) or spermine-biotin-angelicin (SBA: Albarella et al., *Nucleic Acids Res.*, 17:4293–4308 (1989)), BPIMA (Example 18), APIMA (Example 19), AZPIMA (Example 20) or BDA (Example 21) at a concentration of about 100 micromolar.

Example 8

Preparation of Aqueous Solutions for Releasing Nucleic Acid and Amplifying Nucleic Acid This example describes the preparation of aqueous solutions containing lipids for releasing and amplifying nucleic acids.

In the lipid containing formulations of Examples 4, 5(A), (B), (C), and 7, additional chemicals for nucleic acid amplification, which include primers, enzymes and nucleoside triphosphates are added. Formulations with enzymes are made with reagents that are free of proteinases and nucleases. The concentrations of each of the amplification components are adjusted on the basis of type of procedure to be followed. For a typical PCR, a five fold higher concentration of materials is used in formulations so that if one fifth of the mixture is used for amplification the final amplification concentration is adjusted to its optimum level.

Example 9

Preparation of an Aqueous Solution for Releasing and Capturing Nucleic Acid on a Solid Phase This example describes the preparation of aqueous solutions containing lipids for releasing and capturing nucleic acids on a solid phase.

Oligo-dT magnetic particles (Novagen, Madison, Wisconsin) are used as a solid phase for capturing polyA containing RNA from cells. 10 μg of the particles are added to any of Reagents A–D of Examples 5 and 6.

Example 10

Releasing Nucleic Acids from Gram Negative Bacteria Using Aqueous Lipid Solutions E. Coli strain ATCC 35218 (gram negative) is grown in culture medium as described by Isenberg, H. D., (Antimicrobial Susceptibility Testing, ASM press, (1994) pp 5.2.2), to an OD at 600 nm of 1.0, One mL of cell culture is added (in duplicate) to 100 microliters ("μl") of reagent (A) or (B) or (C) or (D) of Example 5. The mixture is incubated at 37° C. for 15 minutes until the absorbency at 600 nm reads less than 0.1 indicating more than 90% lysis.

Example 11

Releasing Nucleic Acids from Gram Positive Bacteria Using Aqueous Lipid Solutions Staphylococcus aureus strain ATCC 29213 (gram positive) is grown as described for E. Coli to an OD at 550 nm of 1.0. One mL of cell culture is added (in duplicate) to 100 microliters ("μl") of reagent (A) or (B) or (C) or (D) of Example 5. The mixture is incubated at 60° C. for 15 minutes until the absorbency at 550 nm reads less than 0.1 indicating more than 90% lysis.

Example 12

Releasing Nucleic Acids from a Clinical Sample Containing Chlamydia Trachomitis

Cervical swabs samples are collected in transport medium (Manual of Clinical microbiology, $5^{TH}$ Ed., ASM press (1991), p1238) lacking any detergent. 0.2 mL of Reagent A described in Example 5 is added to the medium containing the swab. The mixture is incubated at 37° C. for 15 min. 100 μl of the mixture is then subjected to Gen-Probe's commercial PACE 2 assay format (Gen-Probe, Inc., San Diego, Calif.) according to the manufacturer's instructions. The results support efficient release of RNA as judged by the hybridization assay.

Example 13

Releasing, Labeling and Detecting Nucleic acid from a Clinical Sample Suspected of Chlamydial Infection Cervical swabs samples are collected in transport medium lacking any detergent as described in Example 12. 0.2 mL of the aqueous solution containing BPA described in Example 7 is added to the medium containing the swab. The mixture is incubated at 37° C. for 60 minutes. During the incubation step, the sample is exposed to light of 340±30 nm using a transilluminator. After illumination, the labeled sample is hybridized with the PACE 2 probe (Gen-Probe, Inc., San Diego, Calif.), immobilized to nitrocellulose paper. The presence of the label on the nitrocellulose indicates hybridized nucleic acids and demonstrates the effectiveness of the simultaneous lysis and labeling of the released nucleic acids.

Example 14

Releasing Nucleic Acids from a Clinical Sample Infected with Mycobacterium Tuberculosis A sputum sample from a tuberculosis positive individual is processed by treatment with N-Acetyl-L-cysteine-NaOH to generate a sediment as described in the Manual of Clinical microbiology, $5^{th}$ Ed., ASM press (1991), p307–309. 100 μl of the sediment is added to 10 μl of reagent (D) in Example 5 and 90 μl of Tris buffer pH 7.4±0.2. A control extraction sample is prepared containing 100 μl of the sediment and 100 μl of the Tris buffer. The mixtures are incubated at 60° C. for 1 hr and then heated at 90° C. for 15 minutes. The control sample is lysed by sonication. The samples are then tested by PCR as described in Christian et al., *J. Clin. Microbiol.* 33(3):556–561 (1995). The results indicate efficient lysis of both samples.

Example 15

Releasing, Labeling and Detecting Nucleic Acid from a Urine Sample with an Aqueous Lipid Solution This example demonstrates releasing, labeling and detecting nucleic acids from a urine sample with Reagent A of Example 7 (Reagent A contains and BPA as the labeling agent). Urine is processed by centrifugation as described in Dattagupta, et al., *Analytical Biochemistry*, 177:85–89 (1989), and resuspended in 50 mM sodium acetate buffer pH 6. 0.9 mL of the suspension is added to 0.1 mL of Reagent A and the mixture is incubated at 37° C. for 2 hrs. The step of photoactivation and detection of the labeled product is performed as described by Dattagupta, et al. supra (1989). Briefly, after nucleic acid is released (or during incubation), the mixture is exposed to light (365±30 nm) for 60 minutes to conjugate the BPA to the nucleic acid. The labeled nucleic acid is then hybridized to a specific probe.

Example 16

Releasing and labeling Nucleic Acid from a Clinical Serum Sample Suspected of Containing Hepatitis B virus.

This example demonstrates releasing and labeling nucleic acid from a serum sample with an aqueous solution comprising BPA prepared as described in Example 7 (based on any of Regents A–D from Examples 5 or 6) is added to 50%v/v. 100 μl of the serum sample is added to 100 μl of the aqueous solution and the mixture heated at 60° C. for 10 minutes. The step of photoactivation and detection of the labeled product is performed as described by Dattagupta, et al., *Analytical Biochemistry*, 177:85–89 (1989). Briefly, after nucleic acid is released (or simultaneously with incubation), the mixture is exposed to light (365+30 nm) for 60 minutes to conjugate the BPA to the nucleic acid. The labeled nucleic acid is then hybridized to immobilized genomic hepatitis B DNA and detected as described in Dattagupta et al., supra (1989).

Example 17

Preparation of 4'-Biotinyl-pentaoxaheptadecane -4, 5'-dimethylangelicin (BPA)

This example describes the preparation of the photoreactive nucleic acid binding ligand, BPA.

The synthesis of BPA is carried out in the following five steps.

Step 1: Preparation of 3,6,9,12,15-Pentaoxaheptadecane-1, 17-diol ditosylate

A solution of 73.91 g of p-toluenesulfonyl chloride (0.389 mol) in 400 mL of methylene chloride is added dropwise with stirring over a 2.5 hrs period to 400 mL of methylene chloride containing 50 g of hexaethylene glycol (0.177 mol) and 64 mL of triethylamine (39.36 g, 0.389 mol) at 0° C. The mixture is stirred for one hr at 0° C. and heated to ambient temperature for 44 hrs. The mixture is filtered and the filtrate concentrated in vacuo. The resulting residue is suspended in 500 mL of ethyl acetate and filtered. The filtrate is concentrated in vacuo to a yellow oil which was triturated eight times with 250 mL portions of warm hexane to remove unreacted p-toluenesulfonyl chloride. The resulting oil is then concentrated under high vacuum to yield 108.12 g of a yellow oil (quantitative yield).

Analysis: Calculated for $C_{26}H_{38}O_{11}S_2$: Calc.=C, 52.87; H, 6.48. found: C, 52.56; H, 6.39.

PMR ("proton magnetic resonance"): (60 MHz, $CDCl_3$) δ:2.45 (s, 6H); 3.4–3.8 (m, 20H); 4.2 (m, 4H); 7.8 (AB quartet, J=8 Hz, 8H).

IR ("infrared"): (neat) $cm^{-1}$: 2870, 1610, 1360, 1185, 1105, 1020 930, 830, 785, 670.

Step 2: Preparation of 1,17-Diphthalimido 3,6,9,12,15-Pentaoxaheptadecane

A stirred suspension containing 108 g of 3,6,9,12,15-pentaoxaheptadecane-1,17-diol ditosylate (0.183 mol), 74–57 g of potassium phthalimide (0.403 mol), and 700 mL of dimethylacetamide is heated at 160–170° C. for 2 hrs and then cooled to room temperature. The precipitate is filtered and washed with water and acetone to yield 53.05 g of product as a white powder which was dried at 55° C. (0.1 mm); melting point: 124–126° C.

A second crop of product is obtained from the dimethylacetamide filtrate by evaporation in vacuo and the resulting precipitate is successively washed ethyl acetate, water, and acetone. A resulting white powder is dried at 55° C. (0.1 mm of vacuum) to yield an additional 9.7 g of product; melting point 124.5–126.5° C. The combined yield of product is 62.82 g (68% yield).

Analysis: First crop, calculated for $C_{28}H_{32}N_2O_9.1/2H_2O$; Calc.=C, 61.19; H, 6.05; N, 5.09. found: C, 61.08; H. 6.15; N, 5.05.

Second crop calculated for $C_{28}H_{32}N_2O_9$: Calc.=C, 62.21; H, 5.97; N, 5.18. found: C, 61.78; H, 6.15; N, 5.13.

Second Crop PMR: (60 MHz, DMSO-$d_6$) δ: 3.5 (s, 8H); 3.6 (s, 8H); 3.8 (bt, J=3 Hz, 8H); 8.1 (s, 8H).

Second Crop IR: (KBr) $cm^{-1}$: 2890, 1785, 1730, 1400, 1100, 735.

Step 3: Preparation of 1,17-Diamino-3,6,9,12,15-Pentaoxaheptadecane

The synthesis generally followed the method of Kern et al., *Makrol. Chem.*, 180, 2539 (1979). A solution containing 60 g of 1,17-diphthalimido-3,6,9,12,15-pentaoxaheptadecane (0.118 mol), 14.8 g of hydrazine hydrate (0.296 mol), and 500 mL of ethanol is heated with mechanical stirring in a 100° C. oil bath for three hrs. The mixture is cooled and filtered. A resultant filter cake is washed four times with 300 mL portions of ethanol. The combined filtrates are concentrated to yield 32.35 g of a yellow opaque glassy oil by evaporative distillation at 150–200° C. (0.01 mm of vacuum). The result is 22.82 g of a light yellow oil (69% yield). b.p. 175–177° C. (0.07 mm).

Analysis:

For $C_{12}H_{12}N_2O_5.1/2H_2O$: Calc.=C, 49.80, H, 10.10; N, 9.68. found: C, 50.36; H, 9.58; N, 9.38.

PMR: (60 MHz, $CDCl_3$) δ: 1.77 (s, 4H, $NH_2$); 2.85 (t, J=5 Hz, 4H); 3.53 (t, J=5 Hz, 4H); 3.67 (m, 16H).

($CHCl_3$) $cm^{-1}$: 3640, 3360, 2860, 1640, 1585, 1460, 1350, 1250, 1100, 945, 920, 870.

Step 4: Preparation of 1-Amino-17-N-(Biotinylamido)-3,6, 9,12,15-Pentaoxaheptadecane A solution containing 7.2 g of 1,17-diamino-3,6,9,12,15-pentaoxaheptadecane (25 mmol) in 75 mL of dimethylformamide ("DMF") under an argon atmosphere is treated with 3.41 g of N-succinimidyl biotin (10 mmol) added in portions over 1.0 hour. The resulting solution is stirred for four hrs at ambient temperature. A sample of the solution run on TLC ($SiO_2$; solvent: 70:10.1 $CHCL_3$—$CH_3OH$-conc. $NH_4OH$) and visualized by dimethylaminocinnamaldehyde spray reagent to determine conversion to a new product (Rf=0.18). The solution is divided in half and each half absorbed onto $SiO_2$ and purified by flash column chromatography on 500 g of $SiO_2$-60 (230–400 mesh) using a 70:10.1 $CHCl_3$—$CH_3OH$-conc. $NH_4OH$ solvent mixture. Fractions containing the product are pooled and concentrated to a yield 2.42 g of a gelatinous, waxy solid. The product is precipitated as a solid from isopropanol-ether, washed with hexane, and dried at 55° C. (0.1 mm) to result in 1.761 g of a white powder (35% yield).

Analysis:

Calculated for $C_{22}H_{42}N_2O_7.3/2H_2O$: Calc. =C, 49.51; H, 8.50; N. 10.49. found: C, 49.59; H, 8.13; N, 10.39.

PMR: (90 MHz, DMSO-$d_6$) δ: 1.1–1.7 (m, 6H); 2.05 (t, J=7 Hz, 2H); 2.62 (t, J=4 Hz, 1H); 2.74 (t, J=4 Hz, 1H); 3.0–3.4 (m, 14H). 3.50 (s, 14H); 4.14 (m, 1H); 4.30 (m, 1H); 6.35 (d, J=4 Hz, 1H); 7.80 (m, 1H).

CMR: (22.5 MHz, DMSO-$d_6$) δ: 25.2, 28.0, 28.2, 35.1, 40.6, 55.3, 59.2, 61.1, 69.6, 69.8, 71,2, 162.7, 172.1.

IR: (KBr) $cm^{-1}$: 2900, 2850, 1690, 1640, 1580, 1540, 1450, 1100.

Mass Spectrum (FAB) m/e: 507.3 (M+1,56%)

Step 5: Preparation of 4'-Biotinyl-pentaoxaheptadecane 4,5'-dimethylangelicin (BPA)

The synthesis generally followed the method of Albarella, J. P., et al., *Nucl. Acids Res.*, 17:4293 (1989). A solution of 203 mg of 1-amino-17-N(biotinylamido)-3,6,9,12,15-pentaoxaheptadecane(0.4 mmol) in 1 mL of DMF under an argon atmosphere is treated with 78 of N,N-carbonyldimidazole (0.48 mmol). The resulting mixture is stirred for four hrs and then treated with 55 mg of 4'-aminomethyl-4,5' dimethylingelicin hydrochloride (0.2 mmol), 140 μμl of diisopropylethylamine, and 100 μl of DMF. The resulting mixture is stirred overnight at 50° C. and then evaporated onto $SiO_2$ in vacuo and the resultant solid is purified by chromatography on 60 g of $SiO_2$ (230–400 mesh), and eluted with 1.5 liters of 7% $CHCl_3$—$CH_3OH$, followed by 1 liter of 10% $CHCl_3$—$CH_3OH$. Fractions containing the product are pooled and concentrated to yield 72 mg of a glassy solid (47% yield).

Analysis:

PMR: (90 MHz, DMSO-$d_6$):δ. 1.1–1.8 (m, 6H); 2.04 (bt, J=7 Hz, 2H); 2.5 (s, 6H); 2.56 (m, 1H); 2.74 (bd, J=4 Hz,

1H); 2.8–3.4 (m, 14H); 3.40 (m, 14H); 4.14 (m, 1H); 4.25 (m, 1H); 4.40 (bd, J=6 Hz, 2H); 6.5 (m, 1H); 6.35 (s, 1H); 7.02 (s, 1H); 7.45 (d, J=8 Hz, 1H); 7.62 (d, J=8 Hz, 1H); 7.80 (m, 1H).

CMR: (22.5 MHz, DMSO-$d_6$)δ: 11.9, 18.9, 25.3, 28.2 28.3, 33.4, 35.2, 55.4, 59.2, 61.0, 69.2, 69.6, 69.8, 70.0, 89.0, 107.8, 112.0, 113.1, 114.3, 120.6, 121.6, 153.6, 154.4, 155.6. 157.9, 159.5, 162.7, 172.1.

Example 18

Synthesis of Angelicin Bisbenzimidazole-pentaoxaheptadecane-biotin ("BPIMA")

This example describes the preparation of BPIMA, a LAC comprising a photoreactive binding ligand, binding enhancer and a label. The label is biotin and the enhancer moiety is bisbenzimidazole.

The synthesis of BPIMA is carried out in the following eight steps.

Step 1: Synthesis of Dihexadecyl-3-bromo-propanediol

In a 210 mL round bottomed flask equipped with a magnetic stir bar, 2 g of dihexadecylglycerol (Sigma Chem.Co.) is dissolved into 120 mL of toluene. To this solution is added 3.54 g (10.7 mmoles) of carbon tetrabromide and 2.80 g (10.7 mmoles) of tripenylphosphine and the reaction mixture is stirred overnight for 18–20 hrs at room temperature. A resulting yellow suspension is filtered and the filtrate concentrated on a rotary evaporator to afford a white solid residue. This residue is dissolved in toluene, washed once with saturated sodium chloride, dried over anhydrous magnesium sulfate and concentrated under vacuum on a rotary evaporator to afford 2.5 g of crude product as a white powder. This crude product is purified further by flask column chromatography on a silica gel 60 (E. Merck, Germany) column by sequential elution with 100 mL each of hexane, 14 ethyl acetate in hexane, 21 ethyl acetate in hexane and, finally, 31 ethyl acetate in hexane. Fractions (8 mL) are collected and screened by TLC (silica gel; solvent: 5:1 ethyl acetate—hexane) and those fractions that contain pure product are pooled. The pooled fractions are concentrated under vacuum on a rotary evaporator to afford a quantitative yield of 1,2-0-dihexadecyl-3-bromo-1,2 propanediol as a white powder.

Step 2: Synthesis of Bisbenzimidazole Succinate Ester

A solution of bisbenzimidazole (6 g; 0.01 mol) dicyclohexylcarbodiimide (0.05 mol) and Succinic acid (0.01 mol) in 100 mL chloroform is stirred overnight for 18–24 hrs. During this time, a white precipitate is formed. The precipitate is filtered and washed with chloroform (2×50 mL). The chloroform washes are combined and concentrated under vacuum in a rotary evaporator and the residue purified by flash column chromatography. The fractions containing the product are combined and concentrated under vacuum in a rotary evaporate to afford bisbenzimide succinnate ester (80%) as a white solid.

Step 3: Synthesis of pentaoxaheptadecane ditosylate

A solution of p-toluenesufonyl chloride (74 g; 0.39 mol) is added dropwise to a stirred solution containing hexamethylene glycol (50 g; 0.18 mol) trimethylamine (40 g; 0.39 mol) in methylene chloride (400 mL) at 0° C. The reaction mixture is then stirred for 1 hr at room temperature. The mixture is filtered and the filtrate concentrated under vacuum in a rotary evaporator. The residue is suspended in ethylacetate (500 mL) and filtered. The filtrate is concentrated under vacuum to afford yellow oil. The yellow oil is triturated with hexane and the resulting oil vacuum dried to afford 108 g of yellow oil.

Step 4: Synthesis of Diphthalimido pentaoxaheptadecane ditosylate.

A suspension of ditosylate (Step 3;108 g), potassium phthalimide (75 g) in dimethylacetamide (700 mL) is heated at 165° C. for 2 hrs with vigorous stirring. The reaction mixture is then cooled to room temperature and the precipitate filtered. The precipitate is washed with water and acetone to afford 53 g of the desired product as a white solid.

Step 5: Synthesis of Diaminopentaoxaheptadecane (PEG)

A solution of diphthalimide (Step 4:60 g), hydrazine hydrate (15 g) and ethanol (500 mL) is heated at 100° C. with stirring for 3 hrs. The reaction mixture is cooled to room temperature and filtered. The solid is washed with cold ethanol. The combined filtrate is concentrated under vacuum in a rotary evaporator to afford 33 g of yellow oil.

Step 6: Synthesis of 1-Amino-17-N-(Biotinylamido)-pentaoxaheptadecane

A solution of diaminopentaoxaheptadecane (Step 5:7 g) in dimethyformamide is mixed with 3.4 g of N-succinimidylbiotin and then stirred at room temperature for 4 hrs. The product is purified by flash column chromatography on a silica gel 60 column. The fractions containing the product are pooled and concentrated under vacuum in a rotary evaporator to afford 2.5 g of a waxy solid. The waxy solid is recrystallized from isopropanol/ether mixture to afford 1.8 g of white powder.

Step 7: Synthesis of Bisbenzimidazole-PEG-biotin

A solution of biotinylamido pentaoxaheptadecane (Step 6;3 g), bisbenzimidazole succinate ester (Step 2;2 g) and dicydclohexylcarbodimide (5 g) in chloroform (200 mL) is stirred at room temperature for 20–24 hrs. The white precipitate formed is filtered and the precipitate washed with chloroform. The chloroform washes are combined and concentrated under vacuum in a rotary evaporator and the residue purified by flash column chromatography. The fractions containing the product are combined and concentrated under vacuum in a rotary evaporator to afford bisbenzamide-PEG-biotin as an off-white solid (1.5 g).

Step 8: Synthesis of Angelicin bisbenzimidazole-PEG-biotin

To a solution of bisbenzimidazole-PEG-biotin (Step 7;0.4 mmol) in dimethylformamide is added N,N-carbonyldiimidazole (0.5 mmol). The resulting mixture is stirred for 3–5 hrs and is then treated with aminomethylangelicin (0.2 mmol), diisopropylethylamine (150 mL) and dimethylformamide (100 mL). The reaction mixture is stirred overnight at 50–55° C. The mixture is evaporated under vacuum in a rotary evaporator and the residue is loaded onto a column of silica gel and eluted sequentially with 7% methanol in chloroform and 10% methanol in chloroform. The fractions containing the product are pooled and concentrated to afford (0.2 mmol) BPIMA as a glassy solid.

Example 19

Synthesis of Angelicin bisbenzimidazole-pentaoxaheptadecane-acridine ("APIMA")

This example describes the preparation of APIMA, a LAC comprising a photoreactive binding ligand, binding enhancer and label. The label is a chemiluminescent acridinium ester.

The following six steps describes the synthesis of APIMA.

Step 1: Synthesis of Acrdinecarbonylchloride

A solution of acridine carboxyl acid (Aldrich Chem. Co.) and thionyl chloride is stirred at room temperature for 20–24 hrs. Excess thionyl chloride is removed under vacuum in a rotary evaporator. The residue is treated with toluene and evaporated to remove traces of thionyl chloride.

Step 2: Synthesis of Acridine-4-hydroxypropionic Acid Succinimide Ester

A solution of acridine carbonyl chloride(Step 1:2.3 g) in dry pyridine (35 mL) is treated with hydroxyphenolpropionic acid N-hydroxysuccinimide ester (2.5 g) at room temperature for 8–24 hrs. The resulting triethylaminehydochloride is filtered and the solution is concentrated under vacuum in a rotary evaporator to afford the succinimide ester as an off white solid.

Step 3: Synthesis of Methyl Fluorosulfonate Succinimido Acridine

A solution of succinimide ester (Step 2;2 g) and methyl fluorosulfonate (3 mL) in dry chloroform is stirred for 8–24 hrs at room temperature. The resulting solid is filtered and the solution concentrated under vacuum in a rotary evaporator to afford 1.5 g of product as a yellow solid.

Step 4: Synthesis of 1-Amino-17-N(acridnylamido)-pentaoxaheptadecane

A solution of diaminopentaoxaheptadecane (a "PEG": step 5, Example 18) in dimethylformamide (75 mL) is treated with acridine NHS ester (step 3).

The resulting solution is stirred at room temperature for 4 hrs. The solvent is removed under vacuum in a rotary evaporator and the residue is triturated with hexane to afford the compound as a pale yellow solid.

Step 5: Synthesis of Bisbenzimidazole-PEG-acridine

A solution of acridinylamido pentaoxaheptadecane (step 4), bisbenzimidazole succinic acid half ester (step 2, Example 18) and dicyclohexylcarbodimide in chloroform is stirred at room temperature for 18–24 hrs. A white precipitate is filtered and the precipitate washed with chloroform. The combined chloroform washes are concentrated under vacuum in a rotary evaporation to afford the product as an off white solid.

Step 6: Synthesis of angelicin bisbenzimidazole-PEG-acridine

N,N-carbonyldiimidazole is added to a solution of bisbenzimidazole-PEG-acridine (step 5) in dimethylformamide. The resulting mixture is stirred for 3–8 hrs and then treated with aminomethyldimethylangelicin, diisopropylethylamine and dimethylformamide. The mixture is stirred overnight at 50–55° C. and evaporated under vacuum in a rotary evaporator. The residue is purified by flash column chromatography on a column of silica gel. Sequential elution with 7% methanol in chloroform and 10% methanol in chloroform affords fractions containing the product. The fractions are pooled and concentrated to yield APIMA as a solid.

Example 20

Synthesis of Angelicin-bisbenzimidazole-pentaoxaheptadecane-azidonitrobenzene ("AZPIMA")

This example describes the preparation of a AZPIMA, a LAC comprising a photoreactive binding ligand and a binding enhancer, both of which are intercalating moieties.

The following two steps describes the synthesis of AZPIMA.

Step 1: Synthesis of bisbenzimidazole-PEG-azidonitrobenzene

A solution of diaminopentaoxaheptadecane (a "PEG": Step 5, Example 18) and sulfoSANPH® (Pierce Chemicals, Rockford, Ill.) is stirred at room temperature overnight. The solution is concentrated under vacuum in a rotary evaporator and the residue is dissolved in DMF. The solution is treated with bisbenzamide succinate ester (step 2, Example 18) and stirred overnight. Following completion of reaction as determined by TLC, the solution is concentrated to afford an off white crystalline solid.

Step 2: Synthesis of angelicin bisbenzimidazole-PEG-azidonitrobenzene

A solution of bisbenzimidazole-PEG-azidonitrobenzene (Step 1, above) and N,N-carbonyldiimidazole in dimethylformamide is stirred for 4–14 hrs at room temperature. The resulting mixture is treated with aminomethyldimethylangelicin, diisopropylethylamine and the resulting mixture is stirred overnight at 50–55° C. Following completion of reaction, the reaction mixture is concentrated in a rotary evaporator. The residue is purified by flash column chromatography on a column of silica gel. The column. is eluted with a mixture of chloroform/methanol and the fractions containing APIMA are pooled and concentrated to afford APIMA as a solid.

Example 21

Synthesis of Angelicin-4',6'-diamidino-2-phenylindole-Biotin ("BDA")

This example describes the preparation of BDA, as LAC comprising a photoreactive binding ligand, binding enhancer and a label.

The following two steps describes the synthesis of BDA.

Step 1: Synthesis of 1–4',6'-Diamidino-2-phenylindole 17-Pentaoxaheptadecane Tosylate (4',6'-Diamidino-2-phenylindole: "DAPI").

A solution of pentaoxaheptadecane ditosylate (Step 3, Example 18) and DAPI (Aldrich Chem. Co., Cat.No 21,708-5) in dimethylsulfoxide is stirred at room temperature for 8–24 hrs. Upon completion of the reaction, as shown by TLC, the mixture is evaporated under vacuum in a rotary evaporator and the residue loaded onto a column of silica gel and eluted with a solution of 0–50% methanol in chloroform. The fractions containing the product are pooled and concentrated under vacuum in a rotary evaporator to afford the product as an off-white solid.

Step 2: Synthesis of Angelicin-DAPI

A solution of 1-DAPI-17-pentaoxaheptadecane tosylate (step 1) and aminomethyldimethylangelicin in dimthylformamide is stirred at 25–60° C. for 8–48 hrs. Upon completion of the reaction, as shown by TLC, the reaction mixture is evaporated under vacuum in a rotary evaporator and the residue is loaded onto a column of silica gel and eluted with a solution of 0–30% methanol in chloroform containing a trace of ammonia. The fractions containing the product are pooled and concentrated to afford the product as a pale yellow solid. The crude product is recrystallized from a mixture of dimethylformamide and hexane.

Step 3: Synthesis of Angelicin-DAPI-Biotin

A solution of angelicin-DAPI (Step 2) and biotin-NHS ester (Sigma Chem. Co., Cat.No. 1759) in DMF is stirred at 25–70° C. for 8–72 hrs. Upon completion of the reaction, the reaction mixture is evaporated under vacuum in a rotary evaporator and the residue is treated with petroleum ether. The solid is collected by filtration and washed with petroleum ether (3×50 mL). The crude solid is recrystallized to afford BDA as a white solid.

The examples set forth above are provided to give those of ordinary skill in the art with a complete disclosure and description of how to make and use the preferred embodiments of the compositions, and are not intended to limit the scope of what the inventors regard as their invention.

Modifications of the above-described modes for carrying out the invention that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

We claim:

1. A method for detecting the presence of a nucleotide sequence in nucleic acid of a sample, said method comprising the steps of:
   (a) providing an aqueous solution comprising one or more lipids for releasing nucleic acid from the sample, said solution further comprising one or more of:
      i) an enzyme(s) to degrade cell structure;
      ii) a non-ionic membrane fluidizing compound(s); and
      iii) a metal chelator(s);
   wherein said aqueous solution is non-denaturing and non-inhibitory of enzymes or proteins used in and during nucleic acid release, amplification, labeling or detection;
   (b) contacting the sample with the aqueous solution of step a) under conditions suitable for degrading cell structure and releasing the nucleic acid from the cells;
   (c) contacting the nucleic acid with one or more nucleic acid probes or primers that are complementary to the nucleic acid to be detected:
      i) under conditions suitable for the one or more nucleic acid probes to hybridize to the nucleic acid to form a hybridized product; or
      ii) under conditions suitable for amplification of the nucleic acid to form an amplified product; and
   (d) detecting the hybridized product by capture or separation from unhybridized nucleic acid probe and nucleic acid of the sample or detecting the amplified nucleotide sequence, whereby the presence of a nucleotide sequence in nucleic acid of a sample is determined.

2. The method of claim 1, wherein at least a portion of said lipids are in the form of liposomal vesicles having the aqueous solution encapsulated therein.

3. The method of claim 1, wherein said amplification reaction is selected from the group consisting of: polymerase chain reaction, ligase chain reaction, transcription based amplification reaction, nucleic acid sequence based amplification reaction and strand displacement amplification reaction.

4. The method of claim 1, wherein said aqueous solution further comprises a nucleic acid labeling reagent to label the nucleic acid from the cells to facilitate detection of the nucleic acid of the sample subsequent to hybridization, wherein the nucleic acid labeling reagent comprises:
   a binding ligand comprising a chemical moiety that binds to a nucleic acid and that, when activated by light, forms at least one covalent bond therewith and a label comprising a detectable moiety; and
   exposing the nucleic acid labeling reagent and nucleic acid to light of an appropriate length of time and wavelength to cause the binding ligand to become covalently attached to the nucleic acid.

5. The method of claim 4, wherein said nucleic acid labeling reagent further comprises a binding enhancer, wherein said binding enhancer comprises a chemical moiety that has a specific affinity for nucleic acids.

6. The method of claim 4, wherein said aqueous solution further comprises the nucleic acid probes or primers and the nucleic acid labeling reagent, whereby release of nucleic acid and labeling is performed by a single addition of the aqueous solution.

7. The method of claim 1, wherein said nucleic acid probe is labeled to facilitate detection of the nucleotide sequence subsequent to hybridization.

8. The method of claim 1, wherein said sample is a clinical specimen.

9. The method of claim 1, wherein said nucleotide sequence to be detected in the clinical specimen is diagnostic of infectious disease, cancer, a human genetic disorder, or defines genetic profile for forensic, paternity or.

10. A method for detecting the presence of a nucleotide sequence in nucleic acid of a sample, said method comprising the steps of:
   (a) providing an aqueous solution comprising one or more lipids for releasing nucleic acid from the sample, said solution further comprising one or more of:
      i) an enzyme(s) to degrade cell structure; and
      ii) a metal chelator(s);
   wherein said aqueous solution is non-denaturing and non-inhibitory of enzymes or proteins used in and during nucleic acid release, amplification, labeling or detection;
   (b) contacting the sample with the aqueous solution of step a) under conditions suitable for degrading cell structure and releasing the nucleic acid from the cells;
   (c) contacting the nucleic acid with one or more nucleic acid probes or primers that are complementary to the nucleic acid to be detected:
      i) under conditions suitable for the one or more nucleic acid probes to hybridize to the nucleic acid to form a hybridized product; or
      ii) under conditions suitable for amplification of the nucleic acid to form an amplified product; and
   (d) detecting the hybridized product by capture or separation from unhybridized nucleic acid probe and nucleic acid of the sample or detecting the amplified nucleotide sequence, whereby the presence of a nucleotide sequence in nucleic acid of a sample is determined.

11. The method of claim 1, wherein the released nucleic acid is contacted directly with the one or more nucleic acid probes or primers without any dilution, neutralization or separation step subsequent to the releasing step.

* * * * *